(12) United States Patent
Nagase et al.

(10) Patent No.: US 6,337,330 B1
(45) Date of Patent: Jan. 8, 2002

(54) ANTITUSSIVES

(75) Inventors: Hiroshi Nagase; Koji Kawai, both of Kanagawa; Akira Mizusuna, Chiba; Junzo Kamei, Kanagawa, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/254,427

(22) PCT Filed: Jul. 9, 1998

(86) PCT No.: PCT/JP98/03088

§ 371 Date: May 18, 1999

§ 102(e) Date: May 18, 1999

(87) PCT Pub. No.: WO99/02157

PCT Pub. Date: Jan. 21, 1999

(30) Foreign Application Priority Data

Jul. 9, 1997 (JP) ............................................. 9-183842

(51) Int. Cl.[7] ........................ A61K 31/495; A61K 31/44
(52) U.S. Cl. ........................................ 514/250; 514/285
(58) Field of Search ................................. 514/307, 308, 514/297, 250, 285

(56) References Cited

U.S. PATENT DOCUMENTS 5,714,483 A * 2/1998 Nagase et al. ............. 514/229.5

FOREIGN PATENT DOCUMENTS

| JP | 4275288 A | 9/1992 |
| WO | WO 9301186 A1 | 1/1993 |
| WO | 97/10216 * | 3/1997 |

OTHER PUBLICATIONS

Kamei et al, Evidence for Differential Modulation . . . , Neuropahrmacology, 1994, vol. 33/12, pp. 1553–1558.*

* cited by examiner

*Primary Examiner*—William R. A. Jarvis
*Assistant Examiner*—Vickie Kim
(74) *Attorney, Agent, or Firm*—Birch, Stewart, Kolach & Birch, LLP

(57) ABSTRACT

An antitussive agent containing an octahydroisoquinoline derivative represented by the following compound or pharmacologically acceptable acid addition salt thereof:

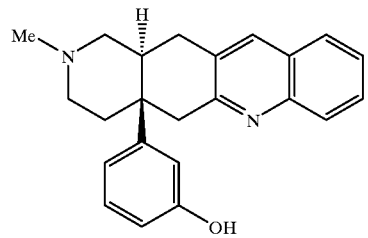

The compounds of the present invention have the significant antitussive action, and can thus be expected as medicines which can be used for all diseases accompanied with coughs, for example, various respiratory diseases such as cold, acute bronchitis, chronic bronchitis, bronchiectasis, pneumonia, pulmonary tuberculosis, silicosis and silicotuberculosis, lung cancer, upper respiratory inflammation (pharyngitis, laryngitis, nasal catarrhalis), asthmatic bronchitis, bronchial asthma, infantile asthma, (chronic) pulmonary emphysema, pneumoconiosis, pulmonary fibrosis, silicosis, pulmonary suppuration, pleurisy, tonsillitis, tussive urticaria, pertussis, etc. and coughs caused in bronchography or bronchoscopy, etc.

8 Claims, 2 Drawing Sheets

ANTITUSSIVES

This application is the national phase under 35 U.S.C. §371 of prior PCT International Application No. PCT/JP98/03088 which has an International filing date of Jul. 9, 1998 which designated the United States of America.

TECHNICAL FIELD

The present invention relates to antitussive application of octahydroisoquinoline derivatives.

BACKGROUND ART

Codeine known as a representative antitussive capable of securely stopping cough acts on opioid $\mu$ receptors to basically cause adverse effects such as drug dependence, respiratory depression, constipation, central inhibition, etc. Therefore, there is demand for a strong antitussive which can be used with safe, and from which the opioid $\mu$ acting adverse effects possessed by codeine are removed.

Although Japanese Unexamined Patent Publication No. 4-275288 discloses compounds of the present invention as opioid δ agonist having a new skeleton, known technologies, including the patent of this publication, do not suggest that the compounds of the present invention having the new skeleton have an antitussive action.

An object of the present invention is to provide a strong antitussive without grave adverse actions such as drug dependence, respiratory depression, constipation, central inhibition, etc.

DISCLOSURE OF INVENTION

The present invention provides an antitussive comprising, as an active component, one of octahydroisoquinoline derivatives represented by the following formula (I) or pharmacologically acceptable acid addition salts thereof, and a therapeutic method using the same.

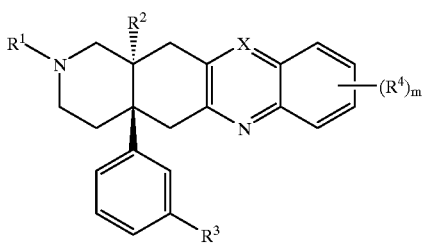

(I)

wherein $R^1$ represents alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 3 to 7 carbon atoms, furan-2-yl-alkyl (wherein an alkyl moiety has 1 to 5 carbon atoms), or thiophene-2-yl-alkyl (wherein an alkyl moiety has 1 to 5 carbon atoms); $R^2$ represents hydrogen, hydroxy, alkoxy having 1 to 5 carbon atoms, or alkanoyloxy having 1 to 5 carbon atoms; $R^3$ represents hydrogen, hydroxy, alkoxy having 1 to 5 carbon atoms, alkanoyloxy having 1 to 5 carbon atoms, or aralkyloxy having 7 to 13 carbon atoms; X represents CH or N; m represents an integer of 0 to 2; m $R^4$ groups independently represent fluorine, chlorine, bromine, iodine, alkyl having 1 to 5 carbon atoms, alkoxy having 1 to 5 carbon atoms, nitro, amino or alkylamino.

BEST MODE FOR CARRYING OUT THE INVENTION

Figure 1:
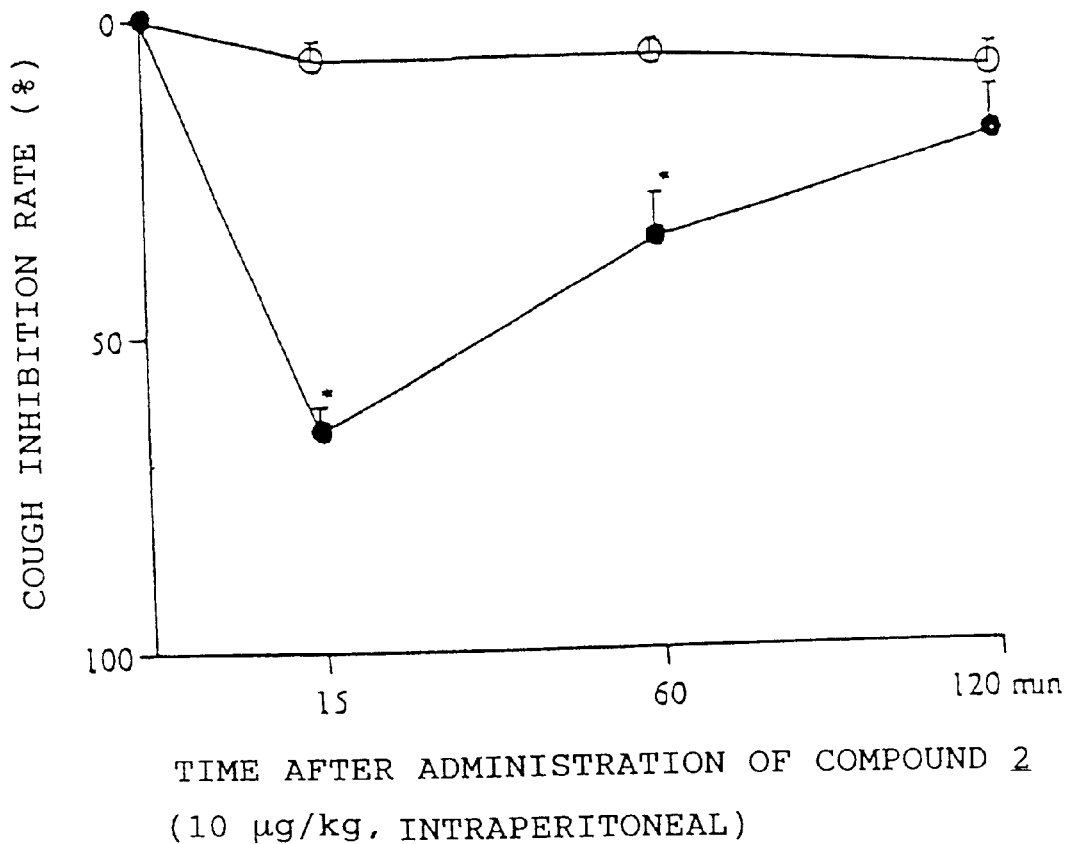
FIG. 1 shows the inhibitory effect of compound 2 on capsaicin-induced cough with time.

Among the compounds of the above formula (I), $R^1$ is preferably hydrogen, alkyl having 1 to 5 carbon atoms, cycloalkylmethyl having 4 to 7 carbon atoms, cycloalkenylmethyl having 5 to 7 carbon atoms, phenyl, naphthyl, phenylalkyl having 7 to 13 carbon atoms, alkenyl having 3 to 7 carbon atoms, furan-2-yl-alkyl (having 1 to 5 carbon atoms), or thiophene-2-yl-alkyl (having 1 to 5 carbon atoms). Particularly, hydrogen, methyl, ethyl, cyclopropylmethyl, cyclobutylmethyl, cyclopentylmethyl, cyclopentenylmethyl, cyclohexenylmethyl, benzyl, phenethyl, trans-2-butenyl, 3-methyl-2-butenyl, allyl, furan-2-yl-methyl, or thiophene-2-yl-methyl is preferred.

$R^2$ is preferably hydrogen, hydroxy, acetoxy, propionoxy, methoxy, or ethoxy. Particularly, hydrogen, hydroxy, acetoxy, or methoxy is preferred.

$R^3$ is preferably hydrogen, hydroxy, acetoxy, propionoxy, methoxy, ethoxy, or benzyloxy. Particularly, hydrogen, hydroxy, acetoxy, methoxy, or benzyloxy is preferred.

$R^4$ is preferably fluorine, chlorine, bromine, alkyl having 1 to 5 carbon atoms, alkoxy having 1 to 5 carbon atoms, nitro, or amino. Particularly, fluorine, chlorine, bromine, methyl, methoxy, nitro, or amino is preferred. Of course, m may be 0, i.e., the compounds may be unsubstituted by $R^4$. Of course, the present invention is not limited to these compounds.

The formula (I) represents the relative arrangement of compounds, and compounds of the present invention include racemic compounds and optically active compounds having absolute structures represented by the following formulae (A) and (B). Particularly, optically active compounds having the absolute structure represented by formula (A) are preferred.

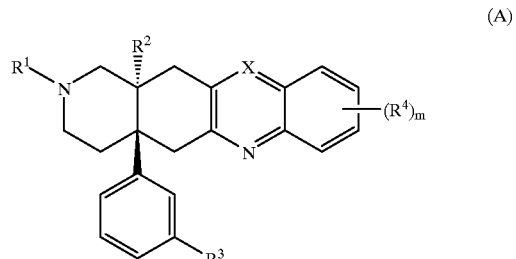

(A)

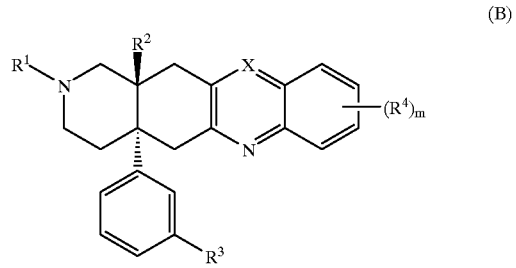

(B)

Pharmacologically preferable acid addition salts include inorganic acid salts such as hydrochlorides, sulfates, nitrates, hydrobromides, hydroiodides, phosphates, and the like; organic carboxylates such as acetates, lactates, citrates, oxalates, glutarates, malates, tartrates, fumarates, mandelates, maleates, benzoates, phthalates, and the like;

organic sulfonates such as methanesulfonates, ethanesulfonates, benzenesulfonates, p-toluenesulfonates, campharsulfonates, and the like. Particularly, hydrochlorides, hydrobromides, phosphates, tartrates, methanesulfonates, and the like are preferably used. However, acid addition salts are not limited to these salts.

Of the compounds of the formula (I) of the present invention, compound 2 having the absolute structure represented by the formula (A) is designated (4aR, 12aR)-2-methyl-4a-(3-hydroxyphenyl)-1,2,3,4,4a,5,12,12a-octahydro-quinolino[2, 3-g]isoquinoline, in which $R^1$ is methyl, $R^2$ is hydrogen, $R^3$ is hydroxy, X is CH, and m is 0.

2

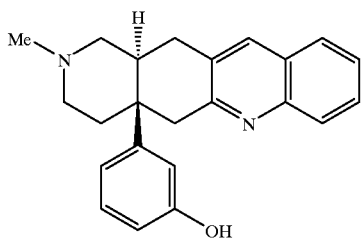

In accordance with the above nomenclature, examples of the compounds of the present invention include: (4aR, 12aR)-2-cyclopropylmethyl-4a-(3-hydroxyphenyl)-1,2,3,4,4a,5,12,12a-octahydro-quinolino[2, 3-g]isoquinoline, (4aR, 12aR)-2-phenethyl-4a-(3-hydroxyphenyl)-1,2,3,4,4a,5,12,12a-octahydro-quinolino[2, 3-g]isoquinoline, (4aR, 12aR)-4a-(3-hydroxyphenyl)-1,2,3,4,4a,5,12,12a-octahydro-quinolino[2, 3-g]isoquinoline, (4aS, 12aR)-2-methyl-4a-(3-hydroxyphenyl)-12a-hydroxy- 1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-1,2,3,4,4a,5,12,12a-octahydro-quinolino[2, 3-g]isoquinoline, (4aS, 12aR)-2-phenethyl-4a-(3-hydroxyphenyl)-12a-hydroxy-1,2,3,4,4a,5,12,12a-octahydro-quinolino[2, 3-g]isoquinoline, (4aS, 12aR)-4a-(3-hydroxyphenyl)-12a-hydroxy-1,2,3,4,4a,5,12,12a-octahydro-quinolino[2, 3-g]isoquinoline, (4aR, 12aR)-2-methyl-4a-(3-hydroxyphenyl)-12a-methoxy-1,2,3,4,4a,5,12,12a-octahydro-quinollno[2, 3-g]isoquinoline, (4aS, 12aR)-2-cyclopropylmethyl-4a-(3-hydroxyphenyl)-12a-methoxy-1,2,3,4,4a,5,12,12a-octahydro-quinolino[2, 3-g]isoquinoline, (4aS, 12aR)-2-phenethyl-4a-(3-hydroxyphenyl)-12a-methoxy-1,2,3,4,4a,5,12,12a-octahydro-quinolino[2, 3-g]isoquinoline, (4aS, 12aR)-4a-(3-hydroxyphenyl)-12a-methoxy-1,2,3,4,4a,5,12,12a-octahydro-quinolino[2, 3-g]isoquinoline, (4aR, 12aR)-2-methyl-4a-phenyl-1,2,3,4,4a,5,12,12a-octahydro-quinolino[2, 3-g]isoquinoline, (4aR, 12aR)-2-cyclopropylmethyl-4a-phenyl-1,2,3,4,4a,5,12,12a-octahydro-quinolino[2, 3-g]isoquinoline, (4aR, 12aR)-2-phenethyl-4a-phenyl-1,2,3,4,4a,5,12,12a-octahydro-quinolino[2, 3-g]isoquinoline, (4aR, 12aR)-4a-phenyl-1,2,3, 4,4a,5,12,12a-octahydro-quinolino[2, 3-g]isoquinoline, (4aS, 12aR)-2 methyl-4a-phenyl-12a-hydroxy-1,2,3,4,4a,5, 12,12a-octahydro-quinolino[2, 3-g]isoquinoline, (4aS, 12aR)-2-cyclopropylmethyl- 4a-phenyl-12a-hydroxy-1,2,3, 4,4a,5,12,12a-octahydro-quinolino[2, 3-g]isoquinoline, (4aS, 12aR)-2-phenethyl-4a-phenyl-12a-hydroxy-1,2,3,4, 4a,5,12,12a-octahydro-quinolino[2, 3-g]isoquinoline, (4aS, 12aR)-4a-phenyl-12a-hydroxy-1,2,3,4,4a,5,12,12a-octahydro-quinolino[2, 3-g]isoquinoline, (4aS, 12aR)-2-methyl-4a-phenyl-12a-methoxy-1,2,3,4,4a,5,12,12a-octahydro-quinolino[2, 3-g]isoquinoline, (4aS, 12aR)-2-cyclopropylmethyl-4a-phenyl-12a-methoxy-1,2,3,4,4a,5, 12,12a-octahydro-quinolino[2, 3-g]isoquinoline, (4aS, 12aR)-2-phenethyl-4a-phenyl-12a-methoxy-1,2,3,4,4a,5, 12,12a-octahydro-quinolino[2, 3-g]isoquinoline, (4aS, 12aR)-4a-phenyl-12a-methoxy-1,2,3,4,4a,5,12,12a-octahydro-quinolino[2, 3-g]isoquinoline, (4aR, 12aR)-2-methyl-4a-(3-methoxyphenyl)-1,2,3,4,4a,5,12,12a-octahydro-quinolino[2, 3-g]isoquinoline, (4aR, 12aR)-2-cyclopropylmethyl-4a-(3-methoxyphenyl)-1,2,3,4,4a,5,12, 12a-octahydro-quinolino[2, 3-g]isoquinoline, (4aR, 12aR)-2-phenethyl-4a-(3-methoxyphenyl)-1,2,3,4,4a,5,12,12a-octahydro-quinolino[2, 3-g]isoquinoline, (4aR, 12aR)-4a-(3-methoxyphenyl)-1,2,3,4,4a,5,12,12a-octahydro-quinolino[2, 3-g]isoquinoline, (4aS, 12aR)-2-methyl-4a-(3-methoxyphenyl)-12a-hydroxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-1, 2,3,4,4a,5,12,12a-octahydro-quinolino[2, 3-g]isoquinoline, (4aS, 12aR)-2-phenethyl-4a-(3-methoxyphenyl)-12a-hydroxy-1,2,3,4,4a,5,12,12a-octahydro-quinolino[2, 3-g]isoquinoline, (4aS, 12aR)-4a-(3-methoxyphenyl)-12a-hydroxy-1,2,3,4,4a,5,12,12a-octahydro-quinolino[2, 3-g]isoquinoline, (4aS, 12aR)-2-methyl-4a-(3-methoxyphenyl)-12a-methoxy-1,2,3,4,4a,5,12,12a-octahydro-quinolino[2, 3-g]isoquinoline, (4aS, 12aR)-2-cyclopropylmethyl-4a-(3-methoxyphenyl)-12a-methoxy-1,2,3,4,4a,5,12,12a-octahydro-quinolino[2, 3-g]isoquinoline, (4aS, 12aR)-2-phenethyl-4a-(3-methoxyphenyl)-12a-methoxy-1,2,3,4,4a, 5,12,12a-octahydro-quinolino[2, 3-g]isoquinoline, (4aS, 12aR)-4a-(3-methoxyphenyl)-12a-methoxy-1,2,3,4,4a,5,12, 12a-octahydro-quinolino[2, 3-g]isoquinoline, (4aR, 12aR)-2-methyl-4a-(3-hydroxyphenyl)-7-fluoro-1,2,3,4,4a,5,12, 12a-octahydro-quinolino[2, 3-g]isoquinoline, (4aR, 12aR)-2-cyclopropylmethyl-4a-(3-hydroxyphenyl)-7-fluoro-1,2,3, 4,4a,5,12,12a-octahvdro-quinolino[2, 3-g]isoquinoline, (4aS, 12aR)-2-methyl-4a-(3-hydroxyphenyl)-12a-hydroxy-7-fluoro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-7-fluoro-1,2,3,4,4a,5,12,12a-octahydro-quinolino[2, 3-g]isoquinoline, (4aR, 12aR)-2-methyl-4a-(3-methoxyphenyl)-7-fluoro-1,2,3,4,4a,5,12, 12a-octahydro-quinolino[2, 3-g]isoquinoline, (4aR, 12aR)-2-cyclopropylmethyl-4a-(3-methoxyphenyl)-7-fluoro-1,2,3, 4,4a, 5,12,12a-octahydro-quinolino[2, 3-g]isoquinoline, (4aS, 12aR)-2-methyl-4a-(3-methoxyphenyl)-12a-hydroxy-7-fluoro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-7-fluoro-1,2,3,4,4a,5,12,12a-octahydro-quinolino[2, 3-g]isoquinoline, (4aR, 12aR)-2-methyl-4a-(3-hydroxyphenyl)-8-fluoro-1,2,3,4,4a,5,12,12a-octahydro-quinolino[2, 3-g]isoquinoline, (4aR, 12aR)-2-cyclopropylmethyl-4a-(3-hydroxyphenyl)-8-fluoro-1,2,3,4, 4a,5,12,12a-octahydro-quinolino[2, 3-g]isoquinoline, (4aS, 12aR)-2-methyl-4a-(3-hydroxyphenyl)-12a-hydroxy-8-fluoro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-8-fluoro-1,2,3,4,4a,5,12,12a-octahydro-quinolino[2, 3-g]isoquinoline, (4aR, 12aR)-2-methyl-4a-(3-methoxyphenyl)-8-fluoro-1,2,3,4,4a,5,12, 12a-octahydro-quinolino[2, 3-g]isoquinoline, (4aR, 12aR)-2-cyclopropylmethyl-4a-(3-methoxyphenyl)-8-fluoro-1,2,3, 4,4a,5,12,12a-octahydro-quinolino[2, 3-g]isoquinoline, (4aS, 12aR)-2-methyl-4a-(3-methoxyphenyl)-12a-hydroxy-8-fluoro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-8-fluoro-1,2,3,4,4a,5,12,12a-octahydro-quinolino[2, 3-g]isoquinoline, (4aR, 12aR)-2-methyl-4a-(3-hydroxyphenyl)-9-fluoro-1,2,3,4,4a,5,12,12a- octahydro-quinolino[2, 3-g]isoquinoline, (4aR, 12aR)-2-cyclopropylmethyl-4a-(3-hydroxyphenyl)-9-fluoro-1,2,3,4,4a,5,12,12a-octahydro-quinolino[2, 3-g]isoquinoline, (4aS, 12aR)-2-methyl-4a-(3-hydroxyphenyl)-12a-hydroxy-9-fluoro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-9-fluoro-1,2,3,4,4a,5,12,12a-octahydro-quinolino[2, 3-g]isoquinoline, (4aR, 12aR)-2-methyl-4a-(3-methoxyphenyl)-9-fluoro-1,2,3,4,4a,5,12,12a-octahydro-quinolino[2, 3-g]isoquinoline, (4aR, 12aR)-2-cyclopropylmethyl-4a-(3-methoxyphenyl)-9-fluoro-1,2,3,4,4a,5,12,12a-octahydro-quinolino[2, 3-g]isoquinoline, (4aS, 12aR)-2-methyl-4a-(3-methoxyphenyl)-12a-hydroxy-9-fluoro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-9-fluoro-1,2,3,4,4a,5,12,12a-octahydro-quinolino[2, 3-g]isoquinoline, (4aR, 12aR)-2-methyl-4a-(3-hydroxyphenyl)-10-fluoro-1,2,3,4,4a,5,12,12a-octahydro-quinolino[2, 3-g]isoquinoline, (4aR, 12aR)-2-cyclopropylmethyl-4a-(3-hydroxyphenyl)-10-fluoro-1,2,3,4,4a,5,12,12a-octahydro-quinolino[2, 3-g]isoquinoline, (4aS, 12aR)-2-methyl-4a-(3-hydroxyphenyl)-12a-hydroxy-10-fluoro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-10-fluoro-1,2,3,4,4a,5,12,12a-octahydro-quinolino[2, 3-g]isoquinoline, (4aR, 12aR)-2-methyl-4a-(3-methoxyphenyl)-10-fluoro-1,2,3,4,4a,5,12,12a-octahydro-quinolino[2, 3-g]isoquinoline, (4aR, 12aR)-2-cyclopropylmethyl-4a-(3-methoxyphenyl)-10-fluoro-1,2,3,4,4a,5,12,12a-octahydro-quinolino[2, 3-g]isoquinoline, (4aS, 12aR)-2-methyl-4a-(3-methoxyphenyl)-12a-hydroxy-10-fluoro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-10-fluoro-1,2,3,4,4a,5,12,12a-octahydro-quinolino[2, 3-g]isoquinoline, (4aR, 12aR)-2-methyl-4a-(3-hydroxyphenyl)-7-chloro-1,2,3,4,4a,5,12,12a-octahydro-quinolino[2, 3-g]isoquinoline, (4aR, 12aR)-2-cyclopropylmethyl-4a-(3-hydroxyphenyl)-7-chloro-1,2,3,4,4a,5,12,12a-octahydro-quinolino[2, 3-g]isoquinoline, (4aS, 12aR)-2-methyl-4a-(3-hydroxyphenyl)-12a-hydroxy-7-chloro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-7-chloro-1,2,3,4,4a,5,12,12a-octahydro-quinolino[2, 3-g]isoquinoline, (4aR, 12aR)-2-methyl-4a-(3-methoxyphenyl)-7-chloro-1,2,3,4,4a,5,12,12a-octahydro-quinolino[2, 3-g]isoquinoline, (4aR, 12aR)-2-cyclopropylmethyl-4a-(3-methoxyphenyl)-7-chloro-1,2,3,4,4a,5,12,12a-octahydro-quinolino[2, 3-g]isoquinoline, (4aS, 12aR)-2-methyl-4a-(3-methoxyphenyl)-12a-hydroxy-7-chloro-1,2,3,4,4a,5,12,12a-octahydro-quinolino[2, 3-g]isoquinoline, ( 4aS, 12aR)-2-cyclopropylmethyl-4a-(3-methoxyphenyl)-12a-hydroxy-7-chloro-1,2,3,4,4a,5,12,12a-octahydro-quinolino[2, 3-g]isoquinoline, (4aR, 12aR)-2-methyl-4a-(3-hydroxyphenyl)-8-chloro-1,2,3,4,4a,5,12,12a-octahydro-quinolino[2, 3-g]isoquinoline, (4aR, 12aR)-2-cyclopropylmethyl-4a-(3-hydroxyphenyl)-8-chloro-1,2,3,4,4a,5,12,12a-octahydro-quinolino[2, 3-g]isoquinoline, (4aS, 12aR)-2-methyl-4a-(3-hydroxyphenyl)-12a-hydroxy-8-chloro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-8-chloro-1,2,3,4,4a,5,12,12a-octahydro-quinolino[2, 3-g]isoquinoline, (4aR, 12aR)-2-methyl-4a-(3-methoxyphenyl)-8-chloro-1,2,3,4,4a,5,12,12a-octahydro-quinolino[2, 3-g]isoquinoline, (4aR, 12aR)-2-cyclopropylmethyl-4a-(3-methoxyphenyl)-8-chloro-1,2,3,4,4a,5,12,12a-octahydro-quinolino[2, 3-g]isoquinoline, (4aS, 12aR)-2-methyl-4a-(3-methoxyphenyl)-12a-hycroxy-8-chloro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-8-chloro-1,2,3,4,4a,5,12,12a-octahydro-quinolino[2, 3-g]isoquinoline, (4aR, 12aR)-2-methyl-4a-(3-hydroxyphenyl)-9-chloro-1,2,3,4,4a,5,12,12a-octahydro-quinolino[2, 3-g]isoquinoline, (4aR, 12aR)-2-cyclopropylmethyl-4a-(3-hydroxyphenyl)-9-chloro-1,2,3,4,4a,5,12,12a-octahydro-quinolino[2, 3-g]isoquinoline, (4aS, 12aR)-2-methyl-4a-(3-hydroxyphenyl)-12a-hydroxy-9-chloro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-9-chloro-1,2,3,4,4a,5,12,12a-octahydro-quinolino[2, 3-g]isoquinoline, (4aR, 12aR)-2-methyl-4a-(3-methoxyphenyl)-9-chloro-1,2,3,4,4a,5,12,12a-octahydro-quinolino[2, 3-g]isoquinoline, (4aR, 12aR)-2-cyclopropylmethyl-4a-(3-methoxyphenyl)-9-chloro-1,2,3,4,4a,5,12,12a-octahydro-quinolino[2, 3-g]isoquinoline, (4aS, 12aR)-2-methyl-4a-(3-methoxyphenyl)-12a-hydroxy-9-chloro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-9-chloro-1,2,3,4,4a,5,12,12a-octahydro-quinolino[2, 3-g]isoquinoline, (4aR, 12aR)-2-methyl-4a-(3-hydroxyphenyl)-10-chloro-1,2,3,4,4a,5,12,12a-octahydro-quinolino[2, 3-g]isoquinoline, (4aR, 12aR)-2-cyclopropylmethyl-4a-(3-hydroxyphenyl)-10-chloro-1,2,3,4,4a,5,12,12a-octahydro-quinolino[2, 3-g]isoquinoline, (4aS, 12aR)-2-methyl-4a-(3-hydroxyphenyl)-12a-hydroxy-10-chloro-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-10-chloro-1,2,3,4,4a,5,12,12a-octahydro-quinolino[2, 3-g]isoquinoline, (4aR, 12aR)-2-methyl-4a-(3-methoxyphenyl)-10-chloro-1,2,3,4,4a,5,12,12a-octahydro-quinolino[2, 3-g]isoquinoline, (4aR, 12aR)-2-cyclopropylmethyl-4a-(3-methoxyphenyl)- 10-chloro-1,2,3,4,4a,5,12,12a-octahydro-quinolino[2, 3-g]isoquinoline, (4aS, 12aR)-2-methyl-4a-(3-methoxyphenyl)-12a-hydroxy-10-chloro-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-10-chloro-1,2,3,4,4a,5,12,12a-octahydro-quinolino[2, 3-g]isoquinoline, (4aR, 12aR)-2-methyl-4a-(3-hydroxyphenyl)-7-bromo-1,2,3,4,4a,5,12,12a-octahydro-quinolino[2, 3-g]isoquinoline, (4aR, 12aR)-2-cyclopropylmethyl-4a-(3-hydroxyphenyl)-7-bromo-1,2,3,4,4a,5,12,12a-octahydro-quinolino[2, 3-g]isoquinoline, (4aS, 12aR)-2-methyl-4a-(3-hydroxyphenyl)-12a-hydroxy-7-bromo-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-7-bromo-1,2,3,4,4a,5,12,12a-octahydro-quinolino[2, 3-g]isoquinoline, (4aR, 12aR)-2-methyl-4a-(3-methoxyphenyl)-7-bromo-1,2,3,4,4a,5,12,12a-octahydro-quinolino[2, 3-g]isoquinoline, (4aR, 12aR)-2-cyclopropylmethyl-4a-(3-methoxyphenyl)-7-bromo-1,2,3,4,4a,5,12,12a-octahydro-quinolino[2, 3-g]isoquinoline, (4aS, 12aR)-2-methyl-4a-(3-methoxyphenyl)-12a-hydroxy-7-bromo-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-7-bromo-1,2,3,4,4a,5,12,12a-octahydro-quinolino[2, 3-g]isoquinoline, (4aR, 12aR)-2-methyl-4a-(3-hydroxyphenyl)-8-bromo-1,2,3,4,4a,5,12,12a-octahydro-quinolino[2, 3-g]isoquinoline, (4aR, 12aR)-2-cyclopropylmethyl-4a-(3-hydroxyphenyl)-8-bromo-1,2,3,4,4a,5,12,12a-octahydro-quinolino[2, 3-g]isoquinoline, (4aS, 12aR)-2-methyl-4a-(3-hydroxyphenyl)-12a-hydroxy-8-bromo-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-8-bromo-1,2,3,4,4a,5,12,12a-octahydro-quinolino[2, 3-g]isoquinoline, (4aR, 12aR)-2- methyl-4a-(3-methoxyphenyl)-8-bromo-1,2,3,4,4a,5,12, 12a-octahydro-quinolino[2, 3-g]isoquinoline, (4aR, 12aR)-2-cyclopropylmethyl-4a-(3-methoxyphenyl)-8-bromo-1,2, 3,4,4a,5,12,12a-octahydro-quinolino[2, 3-g]isoquinoline, (4aS, 12aR)-2-methyl-4a-(3-methoxyphenyl)-12a-hydroxy-8-bromo-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-8-bromo-1,2,3,4,4a,5,12, 12a-octahydro-quinolino[2, 3-g]isoquinoline, (4aR, 12aR)-2-methyl-4a-(3-hydroxyphenyl)-9-bromo-1,2,3,4,4a,5,12, 12a-octahydro-quinolino[2, 3-g]isoquinoline, (4aR, 12aR)-2-cyclopropylmethyl-4a-(3-hydroxyphenyl)-9-bromo-1,2,3, 4,4a,5,12,12a-octahydro-quinolino[2, 3-g]isoquinoline, (4aS, 12aR)-2-methyl-4a-(3-hydroxyphenyl)-12a-hydroxy-9-bromo-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-9-bromo-1,2,3,4,4a,5,12, 12a-octahydro-quinolino[2, 3-g]isoquinoline, (4aR, 12aR)-2-methyl-4a-(3-methoxyphenyl)-9-bromo-1,2,3,4,4a,5,12, 12a-octahydro-quinolino[2, 3-g]isoquinoline, (4aR, 12aR)-2-cyclopropylmethyl-4a-(3-methoxyphenyl)-9-bromo-1,2, 3,4,4a,5,12,12a-octahydro-quinolino[2, 3-g]isoquinoline, (4aS, 12aR)-2-methyl-4a-(3-methoxyphenyl)-12a-hydroxy-9-bromo-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-9-bromo-1,2,3,4,4a,5,12, 12a-octahydro-quinolino[2, 3-g]isoquinoline, (4aR, 12aR)-2-methyl-4a-(3-hydroxyphenyl)-10-bromo-1,2,3,4,4a,5,12, 12a-octahydro-quinolino[2, 3-g]isoquinoline, (4aR, 12aR)-2-cyclopropylmethyl-4a-(3-hydroxyphenyl)-10-bromo-1,2, 3,4,4a,5,12,12a-octahydro-quinolino[2, 3-g]isoquinoline, (4aS, 12aR)-2-methyl-4a-(3-hydroxyphenyl)-12a-hydroxy-10-bromo-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-10-bromo-1,2,3,4,4a,5,12, 12a-octahydro-quinolino[2, 3-g]isoquinoline, (4aR, 12aR)-2-methyl-4a-(3-methoxyphenyl)-10-bromo-1,2,3,4,4a,5,12, 12a-octahydro-quinolino[2, 3-g]isoquinoline, (4aR, 12aR)-2-cyclopropylmethyl-4a-(3-methoxyphenyl)-10-bromo-1,2, 3,4,4a,5,12,12a-octahydro-quinolino[2, 3-g]isoquinoline, (4aS, 12aR)-2-methyl-4a-(3-methoxyphenyl)-12a-hydroxy-10-bromo-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-10-bromo-1,2,3,4,4a,5,12, 12a-octahydro-quinolino[2, 3-g]isoquinoline, (4aR, 12aR)-2,7-dimethyl-4a-(3-hydroxyphenyl)-1,2,3,4,4a,5,12,12a-octahydro-quinolino[2, 3-g]isoquinoline, (4aR, 12aR)-2-cyclopropylmethyl-4a-(3-hydroxyphenyl)-7-methyl-1,2,3,4, 4a,5,12,12a-octahydro-quinolino[2, 3-g]isoquinoline, (4aS, 12aR)-2,7-dimethyl-4a-(3-hydroxyphenyl)-12a-hydroxy-1, 2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-7-methyl-1,2,3,4,4a,5,12,12a-octahydro-quinolino[2, 3-g]isoquinoline, (4aR, 12aR)-2,7-dimethyl-4a-(3-methoxyphenyl)-1,2,3,4,4a,5,12,12a-octahydro-quinolino[2, 3-g]isoquinoline, (4aR, 12aR)-2-cyclopropylmethyl-4a-(3-methoxyphenyl)-7-methyl-1,2,3, 4,4a,5,12,12a-octahydro-quinolino[2, 3-g]isoquinoline, (4aS, 12aR)-2,7-dimethyl-4a-(3-methoxyphenyl)-12a-hydroxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-7-methyl-1,2,3,4,4a,5,12, 12a-octahydro-quinolino[2, 3-g]isoquinoline, (4aR, 12aR)-2,8-dimethyl-4a-(3-hydroxyphenyl)-1,2,3,4,4a,5,12,12a-octahydro-quinolino[2, 3-g]isoquinoline, (4aR, 12aR)-2-cyclopropylmethyl-4a-(3-hydroxyphenyl)-8-methyl-1,2,3,4, 4a,5,12,12a-octahydro-quinolino[2, 3-g]isoquinoline, (4aS, 12aR)-2,8-dimethyl-4a-(3-hydroxyphenyl)-12a-hydroxy-1, 2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-8-methyl-1,2,3,4,4a,5,12,12a-octahydro-quinolino[2, 3-g]isoquinoline, (4aR, 12aR)-2,8-dimethyl-4a-(3-methoxyphenyl)-1,2,3,4,4a,5,12,12a-octahydro-quinolino[2, 3-g]isoquinoline, (4aR, 12aR)-2-cyclopropylmethyl-4a-(3-methoxyphenyl)-8-methyl-1,2,3, 4,4a,5,12,12a-octahydro-quinolino[2, 3-g]isoquinoline, (4aS, 12aR)-2,8-dimethyl-4a-(3-methoxyphenyl)-12a-hydroxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-8-methyl-1,2,3,4,4a,5,12, 12a-octahydro-quinolino[2, 3-g]isoquinoline, (4aR, 12aR)-2,9-dimethyl-4a-(3-hydroxyphenyl)-1,2,3,4,4a,5,12,12a-octahydro-quinolino[2, 3-g]isoquinoline, (4aR, 12aR)-2-cyclopropylmethyl-4a-(3-hydroxyphenyl)-9-methyl-1,2,3,4, 4a,5,12,12a-octahydro-quinolino[2, 3-g]isoquinoline, (4aS, 12aR)-2,9-dimethyl-4a-(3-hydroxyphenyl)-12a-hydroxy-1, 2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-9-methyl-1,2,3,4,4a,5,12,12a-octahydro-quinolino[2, 3-g]isoquinoline, (4aR, 12aR)-2,9-dimethyl-4a-(3-methoxyphenyl)-1,2,3,4,4a,5,12,12a-octahydro-quinolino[2, 3-g]isoquinoline, (4aR, 12aR)-2-cyclopropylmethyl-4a-(3-methoxyphenyl)-9-methyl-1,2,3, 4,4a,5,12,12a-octahydro-quinolino[2, 3-g]isoquinoline, (4aS, 12aR)-2,9-dimethyl-4a-(3-methoxyphenyl)-12a-hydroxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-9-methyl-1,2,3,4,4a,5,12, 12a-octahydro-quinolino[2, 3-g]isoquinoline, (4aR, 12aR)-2,10-dimethyl-4a-(3-hydroxyphenyl)-1,2,3,4,4a,5,12,12a-octahydro-quinolino[2, 3-g]isoquinoline, (4aR, 12aR)-2-cyclopropylmethyl-4a-(3-hydroxyphenyl)-10-methyl-1,2,3, 4,4a,5,12,12a-octahydro-quinolino[2, 3-g]isoquinoline, (4aS, 12aR)-2,10-dimethyl-4a-(3-hydroxyphenyl)-12a-hydroxy-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-10-methyl-1,2,3,4,4a,5,12, 12a-octahydro-quinolino[2, 3-g]isoquinoline, (4aR, 12aR)-2,10-dimethyl-4a-(3-methoxyphenyl)-1,2,3,4,4a,5,12,12a-octahydro-quinolino[2, 3-g]isoquinoline, (4aR, 12aR)-2-cyclopropylmethyl-4a-(3-methoxyphenyl)-10-methyl-1,2,3, 4,4a,5,12,12a-octahydro-quinolino[2, 3-g]isoquinoline, (4aS, 12aR)-2,10-dimethyl-4a-(3-methoxyphenyl)-12a-hydroxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-10-methyl-1,2,3,4,4a,5,12, 12a-octahydro-quinolino[2, 3-g]isoquinoline, (4aR, 12aR)-2-methyl-4a-(3-hydroxyphenyl)-7-methoxy-1,2,3,4,4a,5,12, 12a-octahydro-quinolino[2, 3-g]isoquinoline, (4aR, 12aR)-2-cyclopropylmethyl-4a-(3-hydroxyphenyl)-7-methoxy-1, 2,3,4,4a,5,12,12a-octahydro-quinolino[2, 3-g]isoquinoline, (4aS, 12aR)-2-methyl-4a-(3-hydroxyphenyl)-12a-hydroxy-7-methoxy-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-7-methoxy-1,2,3,4,4a,5,12, 12a-octahydro-quinolino[2, 3-g]isoquinoline, (4aR, 12aR)-2-methyl-4a-(3-methoxyphenyl)-7-methoxy-1,2,3,4,4a,5, 12,12a-octahydro-quinolino[2, 3-g]isoquinoline, (4aR, 12aR)-2-cyclopropylmethyl-4a-(3-methoxyphenyl)-7-methoxy-1,2,3,4,4a,5,12,12a-octahydro-quinolino[2, 3-g]isoquinoline, (4aS, 12aR)-2-methyl-4a-(3-methoxyphenyl)-12a-hydroxy-7-methoxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-7- methoxy-1,2,3,4,4a,5,12,12a-octahydro-quinolino[2, 3-g]isoquinoline, (4aR, 12aR)-2-methyl-4a-(3-hydroxyphenyl)-8-methoxy-1,2,3,4,4a,5,12,12a-octahydro-quinolino[2, 3-g]isoquinoline, (4aR, 12aR)-2-cyclopropylmethyl-4a-(3-hydroxyphenyl)-8-methoxy-1,2,3,4,4a,5,12,12a-octahydro-quinolino[2, 3-g]isoquinoline, (4aS, 12aR)-2-methyl-4a-(3-hydroxyphenyl)-12a-hydroxy-8-methoxy-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-8-methoxy-1,2,3,4,4a,5,12,12a-octahydro-quinolino[2, 3-g]isoquinoline, (4aR, 12aR)-2-methyl-4a-(3-methoxyphenyl)-8-methoxy-1,2,3,4,4a,5,12,12a-octahydro-quinolino[2, 3-g]isoquinoline, (4aR, 12aR)-2-cyclopropylmethyl-4a-(3-methoxyphenyl)-8-methoxy-1,2,3,4,4a,5,12,12a-octahydro-quinolino[2, 3-g]isoquinoline, (4aS, 12aR)-2-methyl-4a-(3-methoxyphenyl)-12a-hydroxy-8-methoxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-8-methoxy-1,2,3,4,4a,5,12,12a-octahydro-quinolino[2, 3-g]isoquinoline, (4aR, 12aR)-2-methyl-4a-(3-hydroxyphenyl)-9-methoxy-1,2,3,4,4a,5,12,12a-octahydro-quinolino[2, 3-g]isoquinoline, (4aR, 12aR)-2-cyclopropylmethyl-4a-(3-hydroxyphenyl)-9-methoxy-1,2,3,4,4a,5,12,12a-octahydro-quinolino[2, 3-g]isoquinoline, (4aS, 12aR)-2-methyl-4a-(3-hydroxyphenyl)-12a-hydroxy-9-methoxy-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-9-methoxy-1,2,3,4,4a,5,12,12a-octahydro-quinolino[2, 3-g]isoquinoline, (4aR, 12aR)-2-methyl-4a-(3-methoxyphenyl)-9-methoxy-1,2,3,4,4a,5,12,12a-octahydro-quinolino[2, 3-g]isoquinoline, (4aR, 12aR)-2-cyclopropylmethyl-4a-(3-methoxyphenyl)-9-methoxy-1,2,3,4,4a,5,12,12a-octahydro-quinolino[2, 3-g]isoquinoline, (4aS, 12aR)-2-methyl-4a-(3-methoxyphenyl)-12a-hydroxy-9-methoxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-9-methoxy-1,2,3,4,4a,5,12,12a-octahydro-quinolino[2, 3-g]isoquinoline, (4aR, 12aR)-2-methyl-4a-(3-hydroxyphenyl)-10-methoxy-1,2,3,4,4a,5,12,12a-octahydro-quinolino[2, 3-g]isoquinoline, (4aR, 12aR)-2-cyclopropylmethyl-4a-(3-hydroxyphenyl)-10-methoxy-1,2,3,4,4a,5,12,12a-octahydro-quinolino[2, 3-g]isoquinoline, (4aS, 12aR)-2-methyl-4a-(3-hydroxyphenyl)-12a-hydroxy-10-methoxy-1,2,3,4,4a,5,12,12a-octahydro-quinolino[2, 3-g]isoquinoline, (4aS, 12aR)-2-cyclopropylmethyl-4a-(3-hydroxyphenyl)-12a-hydroxy-10-methoxy-1,2,3,4,4a,5,12,12a-octahydro-quinolino[2, 3-g]isoquinoline, (4aR, 12aR)-2-methyl-4a-(3-methoxyphenyl)-10-methoxy-1,2,3,4,4a,5,12,12a-octahydro-quinolino[2, 3-g]isoquinoline, (4aR, 12aR)-2-cyclopropylmethyl-4a-(3-methoxyphenyl)-10-methoxy-1,2,3,4,4a,5,12,12a-octahydro-quinolino[2, 3-g]isoquinoline, (4aS, 12aR)-2-methyl-4a-(3-methoxyphenyl)-12a-hydroxy-10-methoxy-1,2,3,4,4a,5,12,12a-octahydro-quinolino[2, 3-g]isoquinoline, (4aS, 12aR)-2-cyclopropylmethyl-4a-(3-methoxyphenyl)-12a-hydroxy-10-methoxy-1,2,3,4,4a,5,12,12a-octahydro-quinolino[2, 3-g]isoquinoline, and the like.

The compounds of the formula (I) of the present invention can be obtained by condensation of ketone compounds (IIa) or diketone compounds (IIb) used as raw materials, and o-aminobenzaldehyde derivatives (IIIa) or o-diaminobenzene derivatives (IIIb) in coexistence with an acid catalyst in a solvent according to the method, for example, disclosed in Japanese Unexamined Patent Publication No. 4-275288. The use of optically active materials as raw materials permit the formation of optically active compounds (Chart 1). For example, optically active compounds of ketone compounds (IIa) can be obtained by the method disclosed in WO91/18901.

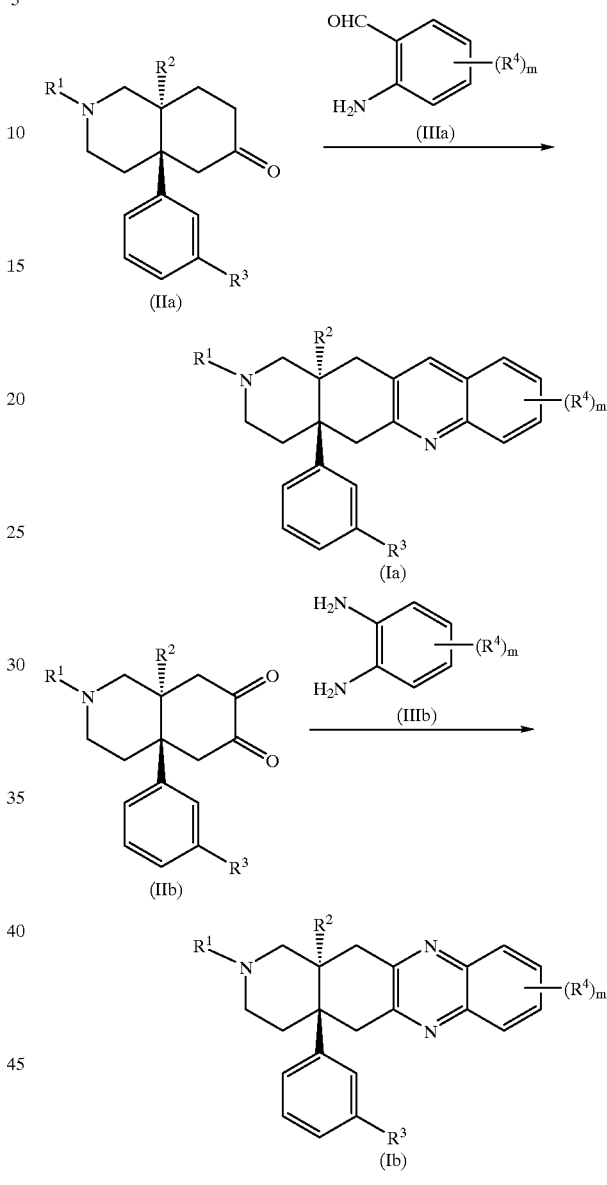

Chart 1

The compounds of the present invention have the strong antitussive action, as shown in Examples, and can be expected as medicines which can be applied to all diseases accompanied with cough, various respiratory diseases such as cold, acute bronchitis, chronic bronchitis, bronchiectasis, pneumonia, pulmonary tuberculosis, silicosis and silicotuberculosis, lung cancer, upper respiratory inflammration (pharyngitis, laryngitis, nasal catarrh), asthmatic bronchitis, bronchial asthma, infantile asthma, (chronic) pulmonary emphysema, pneumoconiosis, pulmonary fibrosis, silicosis, pulmonary suppuration, pleurisy, tonsillitis, tussive urticaria, pertussis, etc. and cough caused in bronchography or bronchoscopy, etc.

The medicines may be clinically used as free bases or salts thereof, and various additives such as an excipient, a stabilizer, a preservative, a buffer, a solubilizer, an emulsifier, a diluent, an isotonizing agent, etc. may be appropriately mixed. As an administration form, either parenteral administration or oral administration may be used. Administration formulations include an injection, a tablet, a liquid, a capsule, granules, a powder, and the like. Although the dosage is appropriately selected in accordance with the symptoms, age and body weight of a patient, the administration method, etc., the amount of the effective component per adult is 0.1 µg to 10 g per day, preferably 1 µg to 1 g per day, and the agent can be administered once or divided into several doses a day.

EXAMPLES

Although the present invention is described in detail below with reference to reference examples and examples, the present invention is not limited to these example.

Reference Example 1

(4aR, 12aR)-2-methyl-4a-(3-methoxyphenyl)-1,2,3,4,4a, 5,12,12a-octahydro-quinolino[2, 3-g]isoquinoline 1

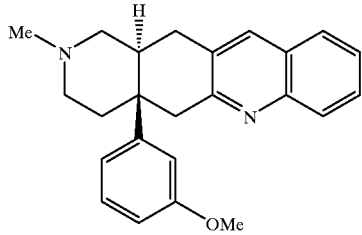

2.00 g (7.32 mmol) of (+)-(4aR, 8aR)-2-methyl-4a-(3-methoxyphenyl)-6-oxo-1,2,3,4,4a,5,6,7,8,8a-decahydroisoquinoline, and 2.66 g (22.0 mmol) of 2-aminobenzaldehyde were dissolved in 60 ml of ethanol under argon, and 1.43 ml (22.0 mmol) of methanesulfonic acid was added to the resultant solution, followed by heating under reflux for 3.5 hours. After the solution was allowed to cool, ethanol was distilled off under reduced pressure, and an aqueous saturated sodium bicarbonate solution was added to the residue to neutralize it, followed by extraction with ethyl acetate. The organic layer was washed with saturated saline, dried, and then concentrated. The thus-obtained residue was isolated and purified by column chromatography [silica gel : chloroform/methanol/28% ammonia aqueous solution (20:1:0.1–10:1:0.1)]. Ether was added to the resultant amorphous product, and the precipitated crystals were filtered off to obtain 1.65 g of title compound. The mother solution was concentrated, and the residue was purified again by column chromatography and crystallization to obtain 0.49 g of title compound (a total of 2.14 g, yield of 82%).

mp: 154–155.5° C. IR (KBr): 2932, 2912, 2806, 1599, 1578, 1493, 1423, 1292, 1247, 1143, 1054, 1036, 878, 777, 758, 700 cm$^{-1}$

NMR (300 MHz, CDCl3): δ 2.02 (1H, td, J=12.6, 3.6 HZ), 2.17 (1H, td, J=12.6, 1.9 Hz), 2.28 (1H, td, J=2.5, 12.6 Hz), 2.39 (3H, s), 2.59–2.80 (3H, m), 2.96 (1H, m), 3.10–3.32 (3H, m), 3.68 (3H, s), 3.75 (1H, d, J=16.5 Hz), 6.58 (1H, m), 7.04–7.10 (3H, m), 7.39 (1H, m), 7.56 (1H, m), 7.64 (1H, d, J=8.2 Hz), 7.78 (1H, s), 7.91 (1H, d, J=8.8 Hz).

EI-MS (m/s): 358 (M+)

Reference Example 2

(4aR, 12aR)-2-methyl-4a-(3-hydroxyphenyl)-1,2,3,4,4a, 5,12,12a-octahydro-quinolino[2, 3-g]isoquinoline 2 methanesulfonate

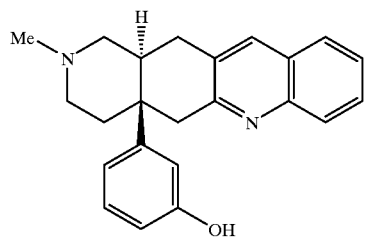

2.00 g (5.58 mmol) of (4aR, 12aR)-2-methyl-4a-(3-methoxyphenyl)-1,2,3,4,4a,5,12,12a-octahydro-quinolino [2, 3-g]isoquinoline obtained in Reference Example 1, and 2.80 ml (30.9 mmol) of n-propanethiol were dissolved in 40ml of DMF under argon, and 3.13 g (27.9 mmol) of potassium-t-butoxide was added to the resultant solution, followed by stirring at 120° C. for 8 hours. 40 ml of 1N hydrochloric acid was added to the solution to acidify it under cooling with ice, and an aqueous saturated sodium bicarbonate solution was added to the solution to alkalify it, followed by extraction with chloroform/methanol (3:1). The organic layer was washed with water, dried and then concentrated. The thus-obtained crude crystals were recrystallized from dichloromethane-methanol-ethyl acetate to obtain 1.61 g title compound (yield 84%). The compound was suspended in methanol, and 900 mg of methanesulfonic acid was added to the resultant suspension to form a salt. After concentration, ether was added to the residue, and the solid was filtered off to obtain 2.37 g of the title compound as methanesulfonate.

mp (free compound): >270° C. (decomposition)

IR (free compound, KBr): 3100, 2940, 1578, 1493, 1448, 1423, 1267, 913, 781, 762, 708 cm$^{-1}$.

NMR (400 MHz, DMSO-d6) δ 2.12 (1H, m), 2.38 (6H, s), 2.56 (1H, m), 2.67 (1H, m), 2.81 (1H, m), 2.87 (3H, s), 3.36–3.52 (5H, m), 3.70 (1H, d, J=12.2 Hz), 3.76 (1H, d, J=17.1 Hz), 6.53 (1H, dd, J=7.8 Hz, 1.5 Hz), 6.92 (1H, s), 6.97 (1H, d, J=8.3 Hz), 7.04 (1H, t, J=7.8 Hz), 7.78 (1H, t, J=7.8 Hz), 7.96 (1H, t, J=8.3 Hz), 8.06 (1H, d, J=8.3 Hz), 8.13 (1H, d, J=8.3 Hz), 8.77 (1H, s), 9.40 (1H, br), 9.74 (1H, s).

EI-MS (free compound, m/z): 344 (M+).

Elementary Analysis: As C23H24N20.2CH3SO3H.0.4H2O

Calculated value: C 55.21, H 6.08, N 5.15, S 11.79

Measured value : C 55.29, H 6.29, N 5.17, S 11.87

Reference Example 3

(4aR, 12aR)-4a-(3-benzyloxyphenyl)-2-vinyloxycarbonyl-1,2,3,4,4a,5,12,12a-octahydroquinolino [2, 3-g]isoquinoline 3

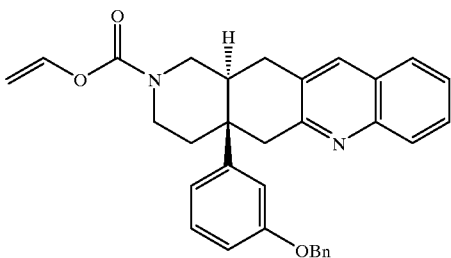

3

Sodium hydride (60%, 79.2 mg) and anhydrous DMF (1 ml) were added to a reactor. A solution of (4aR, 12aR)-4a-(3-hydroxyphenyl)-2-methyl-1,2,3,4,4a,5,12,12a-octahydro-quinolino[2, 3-g]isoquinoline (530 mg, 1.58 mmol) in anhydrous DMF (23 ml), and benzyl bromide (0.20 ml, 1.66 mmol) were added to the reactor, followed by stirring at room temperature for 1 hour. After reaction was completed, an aqueous saturated sodium bicarbonate solution (50 ml), distilled water (50 ml), and toluene (250 ml) were added to the reaction solution, followed by fractionation. The aqueous layer was extracted twice with toluene (150 ml), and the organic layers were together dried over sodium sulfate, filtered, and then concentrated to obtain 531 mg of benzyl ether compound. The thus-obtained compound was supplied to next reaction without purification.

The thus-obtained benzyl ether compound (531 mg) and proton sponge (534 mg, 2.50 mmol) were dissolved in dichloromethane (25 ml), and vinyl chloroformate (0.16 ml, 1.87 mmol) was added dropwise to the resultant solution at 0° C. under an argon stream. After stirring at room temperature for 3 hours, 1N hydrochloric acid (100 ml) was added to the resultant solution, followed by extraction with chloroform (100 ml). The organic layer was washed with 1N hydrochloric acid (100 ml×2 times) and water (100 ml), dried over sodium sulfate, filtered, and then concentrated. The residue was purified by using a silica gel column to obtain a target compound (354 mg, 58% in two steps).

1H-NMR (CDCl3, 300 MHz): δ (ppm) 1.79–1.95 (1H, m), 2.20–2.32 (1H, m), 2.42–2.55 (1H, m), 2.87–3.20 (4H, m), 3.28–3.58 (1H, m), 3.76 (1H, dJ=16.7 Hz), 3.97–4.10 (1H, m), 4.10–4.30 (1H, m), 4.43–4.53 (1H, m), 4.75–4.90 (1H, m), 4.92 (2H, s), 6.65–6.73 (1H, m), 7.00–7.13 (3H, m), 7.22–7.53 (6H, m), 7.59 (1H, m), 7.63 (1H, d, J=9.9 Hz), 7.68 (1H, d, J=1.1 Hz), 7.76 (1H, s), 7.93 (1H, d, J=8.2 Hz).

Reference Example 4

(4aR, 12aR)-4a-(3-hydroxyphenyl)-1,2,3,4,4a,5,12,12a-octahydroquinolino[2, 3-g]isoquinoline 4 methanesulfonate

4

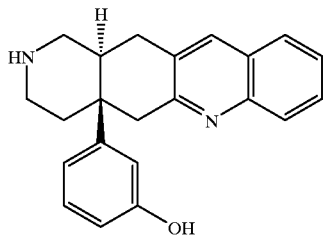

(4aR, 12aR)-4a-(3-benzyloxyphenyl)-2-vinyloxycarbonyl-1,2,3,4,4a,5,12,12a-octahydroquinolino[2, 3-g]isoquinoline (85 mg, 0.17 mmol) was dissolved in acetic acid (4 ml), and conc. hydrochloric acid (2 ml) was added to the resultant solution, followed by stirring at 80° C. for 1 hour. After reaction was terminated, the temperature was returned to room temperature, and a 28% aqueous ammonia solution (10 ml), water (40 ml), methanol (10 ml), and chloroform (40 ml) were added to the reaction solution, followed by fractionation. The aqueous layer was extracted with a chloroform/methanol (=4/1) solvent mixture (50 ml×3 times). The organic layers were together dried, and then concentrated. The residue was purified by a silica gel column to obtain a target substance (32 mg, 56%). Methanesulfonic acid (19 mg) was added to the thus-obtained substance in methanol to form 2-methanesulfonate.

IR (KBr) 3424, 1597, 1442, 1328, 1196, 1058, 785 cm-1.

1H-NMR (DMSO-d6/D20, 500 MHz) δ (ppm) 2.02–2.12 (1H, m), 2.39 (s, 6H), 2.45–2.62 (1H, m), 2.73–2.84 (1H, m), 3.26–3.32 (1H, m), 3.35–3.54 (6H, m), 3.74 (1H, d, J=17.0 Hz), 6.55 (1H, dd, J=2.0, 6.0 Hz), 6.92 (1H, s), 6.97 (1H, d, J=8.1 Hz), 7.06 (1H, dd, J=7.8, 8.0 Hz), 7.78 (1H, dd, J=7.5, 7.7 Hz), 7.95 (1H, dd, J=7.5, 8.1 Hz), 8.03 (1H, d, J=8.6 Hz), 8.12 (1H, d, J=8.2 Hz), 8.71 (1H, s). MS (EI, m/z) 330 (M+) (free compound).

Reference Example 5

(4aR, 12aR)-4a-(3-benzyloxyphenyl)-1,2,3,4,4a,5,12, 12a-octahydroquinolino[2, 3-g]isoquinoline 5

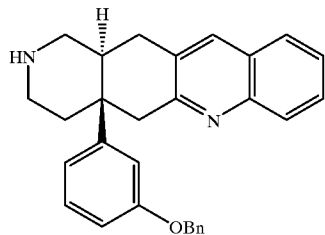

(4aR, 12aR)-4a-(3-benzyloxyphenyl)-2-vinyloxycarbonyl-1,2,3,4,4a,5,12,12a-octahydroquinolino [2, 3-g]isoquinoline (181 mg, 0.369 mmol) was dissolved in a 10% hydrogen chloride methanol solution (6 ml), and the resultant solution was heated under reflux for 1 hour. After the solution was cooled to 0°C., an aqueous saturated sodiumbicarbonate solution (30 ml) and water (150 ml) were added to the solution, followed by extraction with chloroform (200 ml, 2 times). The organic layers were dried, and then concentrated to obtain the target compound (155 mg). The thus-obtained compound was supplied to next reaction without purification.

1H-NMR (CDCl3, 300 MHz) δ (ppm) 1.75–1.90 (1H, m), 1.95 (1H, br, s), 2.17–2.25 (1H, m), 2.37–2.50 (1H, m), 2.66–2.78 (1H, m)), 2.82–2.92 (1H, m), 2.97–3.18 (4H, m), 3.37 (1H, dd, J=12.4, 12.4 Hz), 3.73 (1H, d, J=16.7 Hz), 4.93 (2H, s), 6.64–6.69 (1H, m), 7.04–7.16 (3H, m), 7.28–7.44 (6H, m), 7.53–7.60 (1H, m), 7.61–7.66 (1H, m), 7.72 (1H, s), 7.92 (1H, d, J=8.5 Hz)

Reference Example 6

(4aR, 12aR)-2-cyclopropylmethyl-4a-(3-hydroxyphenyl)-1,2,3,4,4a,5,12,12a-octahydroquinolino[2, 3-g]isoquinoline 6 methanesulfonate (4aR, 12aR)-4a-(3-benzyloxyphenyl)-2-vinyloxycarbonyl-1,2,3,4,4a,5,12,12a-octahydroquinolino

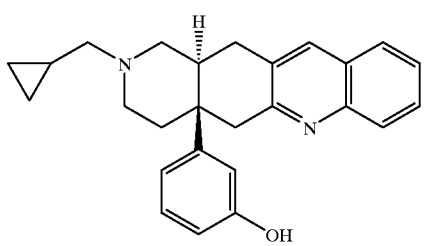

6

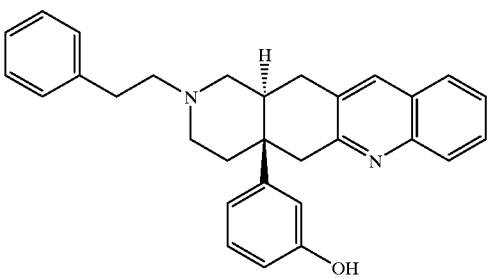

7

(4aR, 12aR)-4a-(3-benzyloxyphenyl)-1,2,3,4,4a,5,12,12a-octahydroquinolino[2, 3-g]isoquinoline (84 mg), and cyclopropanecarboaldehyde (0.0305 ml, 0.40 mmol) were dissolved in dry THF (4 ml), and triacetoxysodium borohydride (84. 8 mg, 0.40 mmol) and acetic acid (0.0126 ml, 0.22 mmol) were added to the resultant solution, followed by stirring at room temperature for 2 hours. A saturated aqueous sodium bicarbonate solution (30 ml) and water (30 ml) were then added to the solution, and the resultant mixture was extracted with chloroform (100 ml, twice). The organic layers were dried over sodium sulfate, and then concentrated. The residue was purified by using a silica gel column to obtain (4aR, 12aR)-2-cyclopropylmethyl-4a-(3-benzyloxyphenyl)-1,2,3,4,4a,5,12,12a-octahydroquinolino[2, 3-g]isoquinoline (78 mg, 82% in two steps).

(4aR, 12aR)-2-cyclopropylmethyl-4a-(3-benzyloxyphenyl)-1,2,3,4,4a,5,12,12a-octahydroquinolino[2, 3-g]isoquinoline (78 mg, 0.163 mmol) was dissolved in acetic acid (3 ml), and conc. hydrochloric acid (1.5 ml) was added to the resultant solution, followed by stirring at 80° C. for 1 hour. After reaction was terminated, the temperature was returned to room temperature, and a 28% aqueous ammonia solution (8 ml), water (50 ml), methanol (10 ml), and chloroform (40 ml) were added to the reaction solution, followed by fractionation. The aqueous layer was extracted with a chloroform/methanol (=4/1) solvent mixture (50 ml×three times), and the organic layers were together dried and then concentrated to obtain a crude product (81 mg). Methanesulfonic acid (36 mg) was added to the thus-obtained crude product in methanol to form 2-methanesulfonate, which was then purified by a Sephadex column to isolate a target compound (55 mg, 59%). IR (KBr) 3407, 1597, 1440, 1197, 1058, 784, 562, 536 cm−1.

1H-NMR (DMSO-d6/D20, 500 MHz) δ (ppm) 0.36–0.46 (1H, m), 0.62–0.73 (1H, m), 1.06–1.14 (1H, m), 2.15–2.20 (1H, m), 2.35 (6H, s), 2.48–2.58 (1H, m), 2.62–2.70 (1H, m), 2.75–2.87 (1H, m), 3.04–3.14 (2H, m), 3.30–3.60 (5H, m), 3.71 (1H, d, J=17.0 Hz), 3.76–3.82 (1H, m), 6.53 (1H, dd, J=1.6, 6.0 Hz), 6.91 (1H, s), 6.94 (1H, d, J=8.2 Hz), 7.00–7.06 (1H, m), 7.72 (1H, dd, J=7.3, 7.5 Hz), 7.88 (1H, dd, J=7.3, 7.9 Hz), 7.97 (1J, d, J=-8.6 Hz), 8.06 (1H, d, J=8.1 Hz), 8.58 (1H, s).
MS (EI, m/z) 384 (M+) (free compound).

Reference Example 7

(4aR, 12aR)-2-(2-phenethyl)-4a-(3-hydroxyphenyl)-1,2,3,4,4a,5,12,12a-octahydroquinolino[2, 3-g]isoquinoline 7 methanesulfonate (4aR, 12aR)-4a-(3-benzyloxyphenyl)-1,2,3,4,4a,5,12,12a-octahydroquinolino[2, 3-g]isoquinoline (71 mg), and phenyl acetoaldehyde (30 to 50% diethyl phthalate solution) (135 mg) were dissolved in dry THF (4 ml)), and triacetoxysodium borohydride (72 mg, 0.34 mmol) and acetic acid (0.011 ml, 0.19 mmol) were added to the resultant solution, followed by stirring at room temperature for 2 hours. A saturated aqueous sodium bicarbonate solution (30 ml) and water (30 ml) were added to the solution, followed by extraction with chloroform (100 ml, twice). The organic layers were dried over sodium sulfate, and then concentrated. The residue was purified by using a silica gel column to obtain (4aR, 12aR)-2-(2-phenethyl)-4a-(3-benzyloxyphenyl)-1,2,3,4,4a,5,12,12a-octahydroquinolino[2, 3-g]isoquinoline (79 mg, 89% in two steps).

(4aR, 12aR)-2-(2-phenethyl)-4a-(3-benzyloxyphenyl)-1,2,3,4,4a,5,12,12a-octahydroquinolino[2, 3-g]isoquinoline (79mg, 0.151mmol) was dissolved in acetic acid (4 ml), and conc. hydrochloric acid (2 ml) was added to the resultant solution, followed by stirring at 80° C. for 1 hour. After reaction was terminated, the temperature was returned to room temperature, and a 28% aqueous ammonia solution (10 ml) and water (50 ml) were added to the reaction solution, followed by three times of extraction with chloroform (50 ml). The organic layers were together dried, and then concentrated. The residue was purified by using a silica gel column to obtain a target compound (60 mg, 91%). Methanesulfonic acid (36 mg) was added to the target compound in methanol to isolate 2-methanesulfate.
IR (KBr) 3423, 1654, 1597, 1440, 1328, 1208, 1191, 1058, 785, 562 cm−1.
1H-NMR (DMSO-d6/D20, 500 NHz) δ (ppm) 2.10 (1H, m), 2.39 (6H, s), 2.55–2.62 (1H, m), 2.71 (1H, dd, J=12.1, 12.6 Hz), 2.78–2.87 (1H, m), 2.99–3.10 (1H, m), 3.35–3.47 (5H, m), 3.51–3.60 (2H, m), 3.73 (1H, d, J=17.0 Hz), 3.81–3.86 (1H, m), 6.73–6.78 (1H, m), 6.91 (1H, s), 9.98 (1H, d, J=8.2Hz), 7.06 (1H, dd, J=7.8, 8.0 Hz), 7.25–7.40 (5H, m), 7.76 (1H, dd, J=7.5, 7.7 Hz), 7.92 (1H, dd, J=7.1, 8.2 Hz), 8.00 (1H, d, J=8.6 Hz), 8.11 (1H, d, J=8.4 Hz), 8.67 (1H, s).
MS (EI, m/z) 434 (M+) (free compound).

Example 1
Evaluation of Antitussive Action Using Mouse Model of Capsaicin-induced Cough
<Induction of cough>
Capsaicin (30 μM) was sent as aerosol to a cap attached to the head of a mouse by using an ultrasonic nebulizer and an artificial respiratory apparatus through a silicon tube, and inhaled by the mouse to induce coughs. For inhalation of capsaicin, capsaicin was sent by using the artificial respiratory apparatus at a rate of 60 times per minute in a dose of 5 ml at a time.

<Experimental Schedule>

15 minutes before administration of a medicine, capsaicin was inhaled for 3 minutes, and it was confirmed that coughs were induced during this time. 15 minutes, 60 minutes and 120 minutes after administration of a medicine, capsaicin was inhaled for 3 minutes to measure the number of coughs induced during this time. The antitussive effect was evaluated by determining the inhibition rate shown by the number of coughs after administration of a medicine based on the number of coughs before administration of a medicine. Capsaicin was dissolved in 10% ethanol and a 10% Tween 80 solution, and diluted with physiological saline. The medicine was dissolved in physiological saline, and intraperitoneally administered.

<Effect of compound 2>

Coughs were stably induced at a rate of 22.5±1.2/3 min. by inhalation of capsaicin. The coughs were not changed by administering physiological saline. The significant effect of suppressing coughs was observed by administering compound 2 (10 µg/kg) with the peak observed 15 minutes after administration, and the antitussive effect decreased with the passage of time. 120 minutes after administration, the effect was recovered to the same level as a group in which physiological saline was administered. The results are shown in FIG. 1. In the figure, each value indicates the inhibition rate shown by the number of coughs, which represents an average ±SE of nine samples. Each of the symbols represents the following:

○: group in which physiological saline was administered
 ●: group in which 10 µg/kg of compound 2 was administered (intraperitoneally) p1 *: p<0.05 versus group in which physiological saline was administered (U test)

Figure 2:
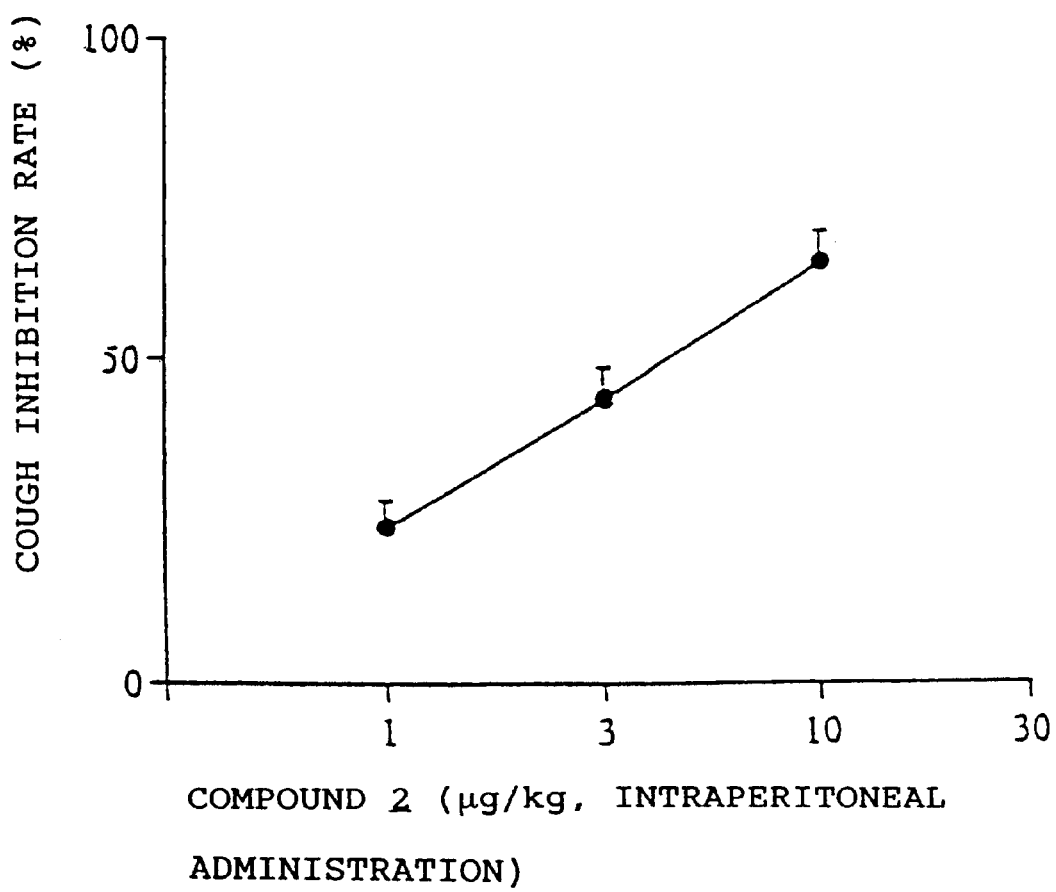
FIG. 2 shows a dose-response curve of the rate of cough inhibition 15 minutes after administration of compound 2.

FIG. 2 shows the dose response of the antitussive effect of compound 2 fifteen minutes after administration. In the figure, each value indicates the inhibition rate shown by the number of coughs, which represents an average ±SE of ten samples. The ED50 value of the antitussive effect of compound 2, which was calculated from FIG. 2, was 4.2 (4.1–4.4) µg/kg.

Example 2
Evaluation of Antitussive Action Using Rat Model of Capsaicin-induced Cough Rat groups each consisting of 5 SD male rats (Charles River Japan) of 7 weeks old were used. The rats not anesthetized were placed in a container comprising two acrylic cylinders including a head and a body. A rubber collar and plastic collar were put on each of the rats, and the head and body of the container were independently provided.

Capsaicin used as a medicine for inducing coughs was aerosolized by an ultrasonic nebulizer, and inhaled by the rats from the front side of the container by using an artificial respiration apparatus. The concentration of capsaicin was 60 µM. In this inhalation, the flow rate of air was 10 ml×70 times/min (700 ml/min). Changes in internal pressure of the closed body box were recorded on a recorder through a differential transducer. Coughs were measured by the changes in internal the body box and visually observing the motions of the rats.

A medicine was diluted with distilled water, and 1 to 10 mg/5 ml/kg was subcutaneously administered.

Each of the rats was fixed by a holder, and 60 minutes after, capsaicin was inhaled for 3 minutes to count the number of coughs. The rats having at least 9 coughs were subjected to examination of a medicine. The rats were administered subcutaneously with a medicine, and fixed by a holder, and 30 minutes after, capsaicin was inhaled for 3 minutes to count the number of coughs. The antitussive action of each of compounds was represented by the inhibition rate shown by the number of coughs of the group in which a medicine was administered based on the number of coughs of the group in which distilled water was administered.

| Compound | Dose (mg/kg) | Inhibition rate (%) |
|---|---|---|
| 2 | 1 | 72.5 |
| 4 | 10 | 34.0 |
| 6 | 1 | 30.9 |
| 7 | 1 | 44.3 |

Industrial Applicability

The compounds of the present invention have the significant antitussive action. Therefore, the compounds and pharmacologically acceptable acid addition salts thereof can be expected as medicines which can be used for all diseases accompanied with coughs, for example, various respiratory diseases such as cold, acute bronchitis, chronic bronchitis, bronchiectasis, pneumonia, pulmonary tuberculosis, silicosis and silicotuberculosiser, lung cancer, upper respiratory inflammation (pharyngitis, laryngitis, nasal catarrh), asthmatic bronchitis, bronchial asthma, infantile asthma, (chronic) pulmonary emphysema, pneumoconiosis, pulmonary fibrosis, silicosis, pulmonary suppuration, pleurisy, tonsillitis, tussive urticaria, pertussis, etc. and coughs caused in bronchography or bronchoscopy, etc.

What is claimed is:

1. A cough preventing method comprising administering, to a patent having a cough, a medicine comprising as an active component an optically active octahydroisoquinoline derivative having absolute structure represented by the following formula (A), or a pharmacologically acceptable acid addition salt thereof:

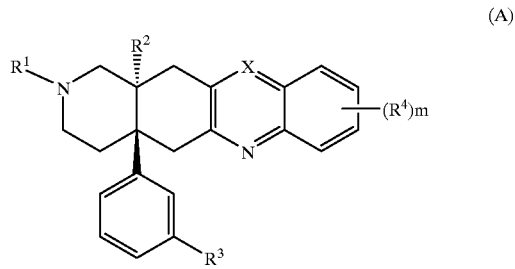

(A)

wherein Rrepresents alkyl having 1 to 5 carbon atoms, cycloalkylalkyl having 4 to 7 carbon atoms, cycloalkenylaLkyl having 5 to 7 carbon atoms, araliyl having 7 to 13 carbon atoms, alkenyl having 3 to 7 carbon atoms, furan-2-yl-alkyl (wherein an alkyl moiety has 1 to 5 carbon atoms), or thiophene-2-yl-alkyl (wherein an alkyl moiety has 1 to 5 carbon atoms);

$R^2$ represents hydrogen, hydroxy, alkoxy having 1 to 5 carbon atoms, or alkanoyloxy having 1 to 5 carbon atoms;

$R^3$ represents hydrogen, hydroxy, alkoxy having 1 to 5 carbon atoms, alkanoyloxy having 1 to 5 carbon atoms, or aralkyloxy having 7 to 13 carbon atoms;

X represents CH or N;

m represents an integer of 0 to 2; and m $R^4$ groups independently represent fluorine, chlorine, bromine, iodine, alkyl having 1 to 5 carbon atoms, alkoxy having 1 to 5 carbon atoms, nitro, amino or alkylamino.

2. A cough preventing method according to claim 1, wherein $R^1$ represents hydrogen, alkyl having 1 to 5 carbon atoms, cycloalkylmethyl having 4 to 7 carbon atoms, cycloalkenylmethyl having 5 to 7 carbon atoms, phenyl, naphthyl, phenylalkyl having 7 to 13 carbon atoms, alkenyl having 3 to 7 carbon atoms, furan-2-yl-alkyl (wherein an alkyl moiety has 1 to 5 carbon atoms), or thiophene-2-yl-alkyl (wherein an alkyl moiety has 1 to 5 carbon atoms).

3. A cough preventing method according to claim 1, wherein $R^1$ represents hydrogen, methyl, ethyl, cyclopropylmethyl, cyclobutylmethyl, cyclopentylmethyl, cyclopentenylmethyl, cyclohexenylmethyl, benzyl, phenethyl, trans-2-butenyl, 3-methyl-2-butenyl, allyl, furan-2-yl-methyl, or thiophene-2-yl-methyl.

4. A cough preventing method according to claim 1, wherein $R^2$ represents hydrogen, hydroxy, acetoxy, or methoxy.

5. A cough preventing method according to claim 1, wherein $R^3$ represents hydrogen, hydroxy, acetoxy, methoxy, or benzyloxy.

6. A cough preventing method according to claim 1, wherein $R^4$ represents fluorine, chlorine, bromine, methyl, methoxy, nitro, or amino.

7. A cough preventing method according to claim 1, wherein m is 0.

8. A cough preventing method according to claim 1, wherein the octahydroisoquinoline derivative is (4aR, 12aR)-2-methyl-4a-(3-hydroxyphenyl)-1,2,3,4,4a,5,12,12a-octahydro-quinolino[2, 3-g]-isoquinoline, or a pharmacologically acceptable acid addition salt thereof.

* * * * *